United States Patent
Lee et al.

(10) Patent No.: US 7,759,111 B2
(45) Date of Patent: Jul. 20, 2010

(54) CELL ENCAPSULATION MICROFLUIDIC DEVICE

(75) Inventors: Abraham Phillip Lee, Irvine, CA (US); Jeffrey S. Fisher, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 370 days.

(21) Appl. No.: 11/215,352

(22) Filed: Aug. 29, 2005

(65) Prior Publication Data

US 2006/0051329 A1 Mar. 9, 2006

Related U.S. Application Data

(60) Provisional application No. 60/605,010, filed on Aug. 27, 2004.

(51) Int. Cl.
*C12M 1/00* (2006.01)
*C12N 11/04* (2006.01)

(52) U.S. Cl. .................................. 435/283.1; 435/182

(58) Field of Classification Search ....................... None
See application file for complete search history.

(56) References Cited

U.S. PATENT DOCUMENTS 6,951,632 B2 * 10/2005 Unger et al. ................. 422/100

FOREIGN PATENT DOCUMENTS

WO  WO 2004/071638 A2 *  8/2004

OTHER PUBLICATIONS

Chang, *Science*, vol. 146, pp. 524-525 (Oct. 23, 1964).
Lim et al., *Science*, vol. 210, pp. 908-909 (Nov. 21, 1980).
Anna et al., *Formation of dispersions using "flow focusing" in microchannels*, Applied Physics Letters, vol. 82, No. 3, pp. 364-366 (Jan. 20, 2003).
Yung-Chieh Tan et al., *Design of microfluidic channel geometries for the control of droplet volume, chemical concentration, and sorting*, Minaturisation for Chemistry, Biology & Bioengineering,. Lap Chip, 2004, 4, pp. 292-298.
Song et al., *A Microfluidic System for Controlling Reaction Networks in Time*, Communications, Angew. Chem. Int. Ed., 2003, vol. 42, No. 7, pp. 767-772.
Kuhtreiber, et al., *Cell Encapsulation Technology and Therapeutics*, Birkhauser, Boston (1999) contents, index, pp. 247-248.
Thorsen, et al., *Dynamic Pattern Formation in a Vesicle-Generating Microfluidic Device*, Physical Review Letters, vol. 86, No. 18, pp. 4163-4166 (Apr. 30, 2001).

* cited by examiner

*Primary Examiner*—David M Naff
(74) *Attorney, Agent, or Firm*—Orrick, Herrington & Sutcliffe LLP

(57) ABSTRACT

Devices and methods for the encapsulation of cells on microfluidic platforms are disclosed. The microfluidic device generally includes a plurality of functional regions to shear, focus, and encapsulate a desired cell or group of cells into a droplet. The microfluidic device can further comprise a polymerization zone to form a polymer bead around the droplet.

2 Claims, 16 Drawing Sheets

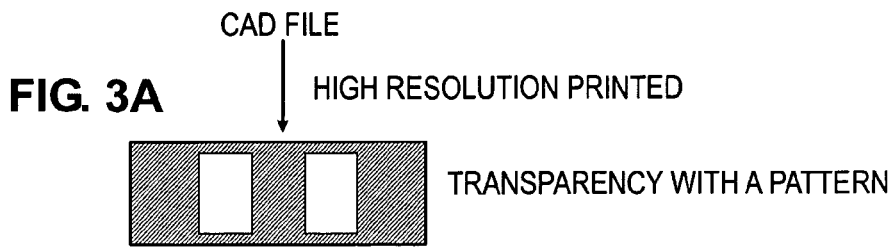
FIG. 3A
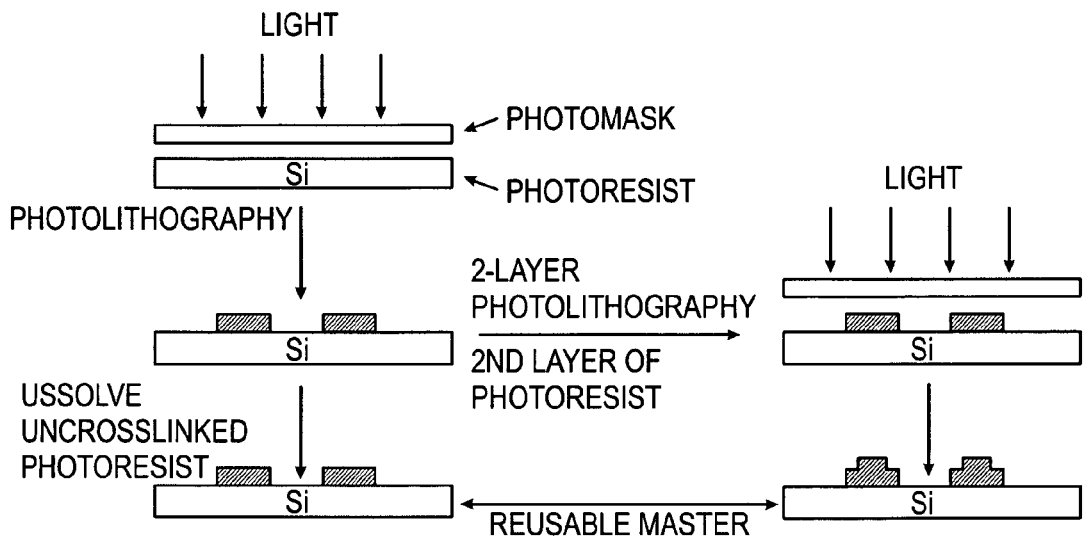
FIG. 3B
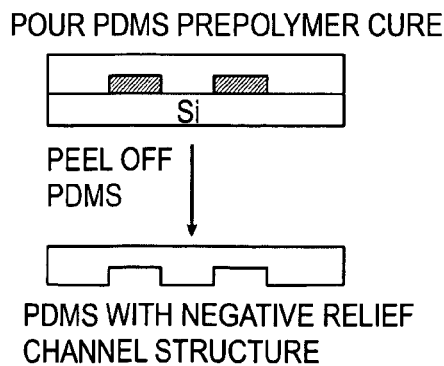
FIG. 3C
FIG. 3D

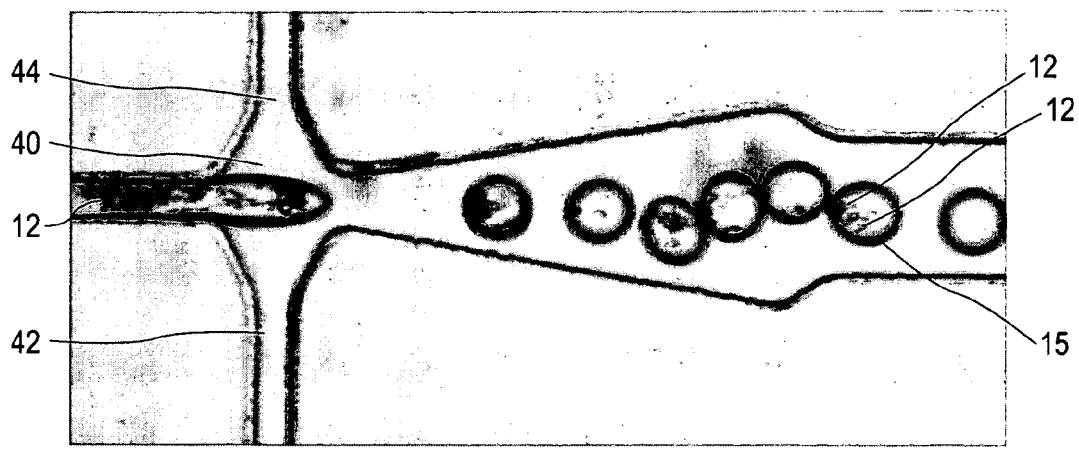
FIG. 12
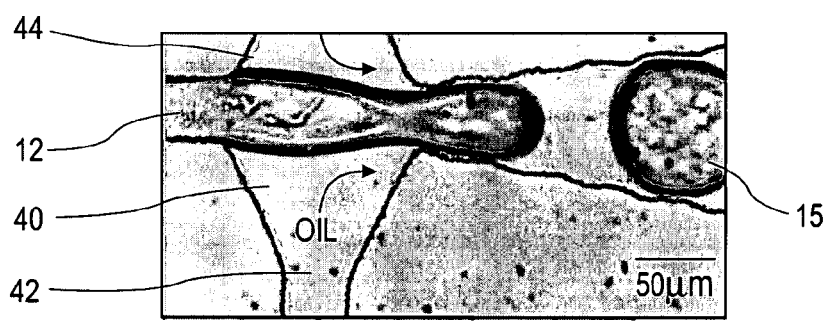
FIG. 13A
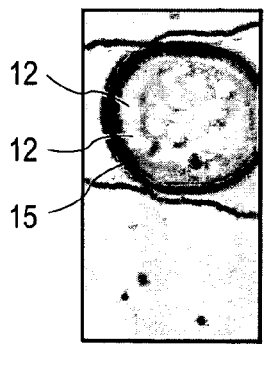  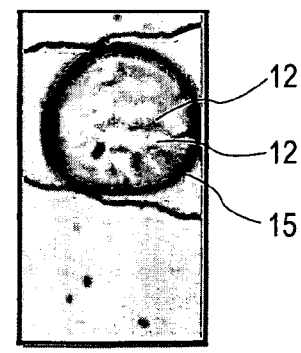
FIG. 13B  FIG. 13C  FIG. 13D

CELL ENCAPSULATION MICROFLUIDIC DEVICE

CROSS REFERENCE TO RELATED APPLICATIONS

This application claims the benefit of U.S. provisional application No. 60/605,010 filed Aug. 27, 2004, the disclosure of which is hereby incorporated by reference.

FIELD OF THE INVENTION

The present invention relates to cell encapsulation and, more particularly, to a microfluidic device for the encapsulation and polymerization of cells with low cell densities in which individual cells are not adhered to one another, and higher cell densities in which the cells form clusters that may be larger than the channel dimensions.

BACKGROUND OF THE INVENTION

Bioencapsulation, which has provided a range of promising therapeutic treatments for diabetes, hemophilia, cancer, and renal failure, emerged as a new area for research for biomedical engineering in 1964 with the use of ultrathin polymer membrane microcapsules, or "artificial cells", for the immunoprotection of transplanted cells. [Chang, Science 146, 524-525 (1964)]. Twenty years later, bioencapsulation was successfully implemented to mobilize xenograft islet cells. When implanted in a rat [Lim et al., Science 210, 908-909 (1980)], the microencapsulated islet corrected the diabetic state for several weeks. Since then, there has been significant progress towards understanding the biological and technological requirements for successful transplantation of encapsulated cells in vivo.

Cell encapsulation has traditionally been accomplished by extruding the droplets carrying the cells through a nozzle (air/water emulsion) into a bath containing the polymerizing agent. These methods have their disadvantages including, e.g., a minimum droplet size, an increase in size dispersion for small droplet sizes, an inability to trap the droplets before (or without) polymerization, and non-uniform polymerization times across droplet population.

FIG. 1 provides an illustration of current encapsulation methods in which capsules are formulated by droplet extrusion or emulsification. In the extrusion techniques, often referred to as the drop method, solutions are extruded through a small tube or needle, permitting the formed droplets to freely fall into a gelation bath. The droplets are cross-linked by addition of appropriate reagent to the receiving solution. A typical example is the formation of alginate beads by dropping a sodium alginate solution into a bath containing calcium chloride. In the emulsion technique, solutions are mixed and dispersed in a non-miscible phase often facilitated with a surfactant. When the dispersion reaches the equilibrium, gelating and/or membrane formation is initiated by cooling and/or addition of gelling agent to the emulsion, or by introduction of a cross-linked agent. These methods produce larger droplets. Also, droplets formed by the extrusion method have different membrane thickness and size as they drop in the gelation bath at different time.

Thus, it would be desirable to provide improved apparatus and methods for the encapsulation of cells with low and high cell densities.

SUMMARY OF THE INVENTION

Described below are exemplary systems and methods of encapsulating and polymerizing cells using microfluidic devices. These systems and methods are examples only and are not intended to limit the invention.

The present invention provides a microfluidic device for the encapsulation and polymerization of cells, for use with low cell densities, in which individual cells are not adhered to one another, and higher densities, in which the cells form clusters that may be larger that the channel dimensions. The cells along with their water-based media are dispersed as droplets into a continuous oil phase. Through droplet fusion, the cells can be rapidly, combinatorially exposed to various drugs or chemical factors. The droplets can be used for automating clonal culturing, and droplets containing different types of cells can be fused to form well-defined, heterogeneous populations.

In one embodiment, a microfluidic device preferably comprises two functional regions: the first region comprising upstream cell loading and shearing zones and the second region comprising a downstream cell encapsulation zone. As the cells pass through the two functional regions, the first region focuses the cells to the center of the channel and shears off cells if they are self-adhered, and the second region encapsulates the cells in droplets. The orientation of the input channels can be modified in order to produce desired droplet characteristics.

The number of cells encapsulated in this way has been estimated to be 20-50 cells per droplet with droplets sizes as small as 20 um in diameter. Droplets can also be polymerized using various on-chip techniques.

The advantages of the apparatus and methods provided herein include much smaller minimum droplet size (~20 µm or less), mono-dispersity of size, ability to trap the droplets before (or without) polymerization, and uniform polymerization times across droplet population due to continuous (rather than batch) nature of the process.

Other systems, methods, features, and advantages of the invention will be or will become apparent to one with skill in the art upon examination of the following figures and detailed description. It is intended that all such additional systems, methods, features and advantages be included within this description, be within the scope of this invention, and be protected by the accompanying claims. It will be understood that the particular methods and apparatus are shown by way of illustration only and not as limitations. As will be understood by those skilled in the art, the principles and features explained herein may be employed in various and numerous embodiments.

BRIEF DESCRIPTION OF THE DRAWINGS

FIG. 3 is a schematic showing fabrication methodologies for the production of a microfluidic device of the present invention.

FIG. 12 is a photograph of the encapsulation region of a microfluidic device of the present invention demonstrating encapsulation of multiple cells.

FIG. 13A is a photograph of the encapsulation region of a microfluidic device of the present invention.

FIGS. 13B-D are photographs of droplets formed in the encapsulation region of FIG. 13A demonstrating encapsulation of multiple adhered cell clusters.

Figure 1:
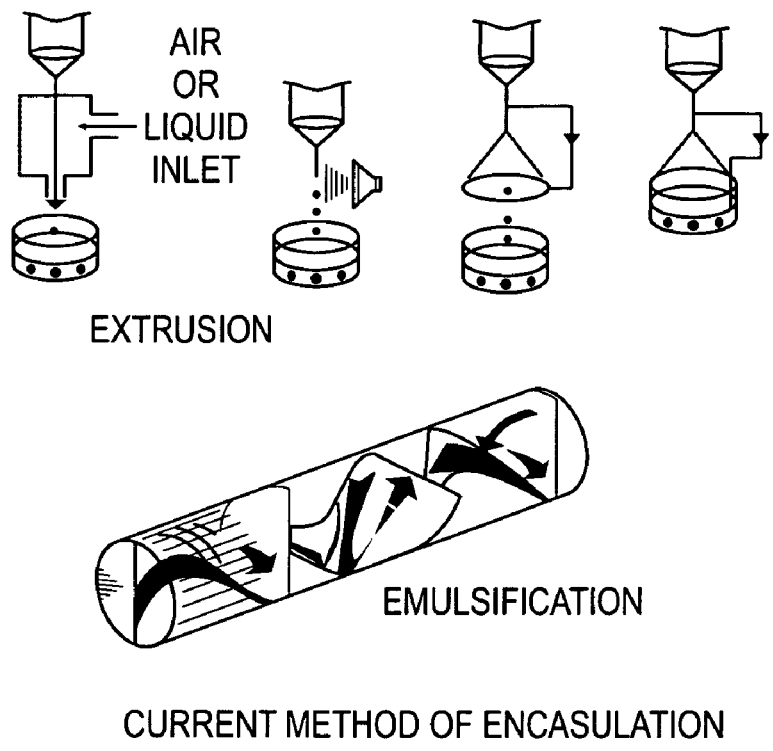
FIG. 1 is a schematic showing current encapsulation methodology.

It should be noted that the figures are not drawn to scale and that elements of similar structures or functions are generally represented by like reference numerals for illustrative purpose throughout the figures. It should also be noted that the figures are only intended to facilitate the description of the preferred embodiments.

DETAILED DESCRIPTION OF THE PREFERRED EMBODIMENTS

Figure 2:
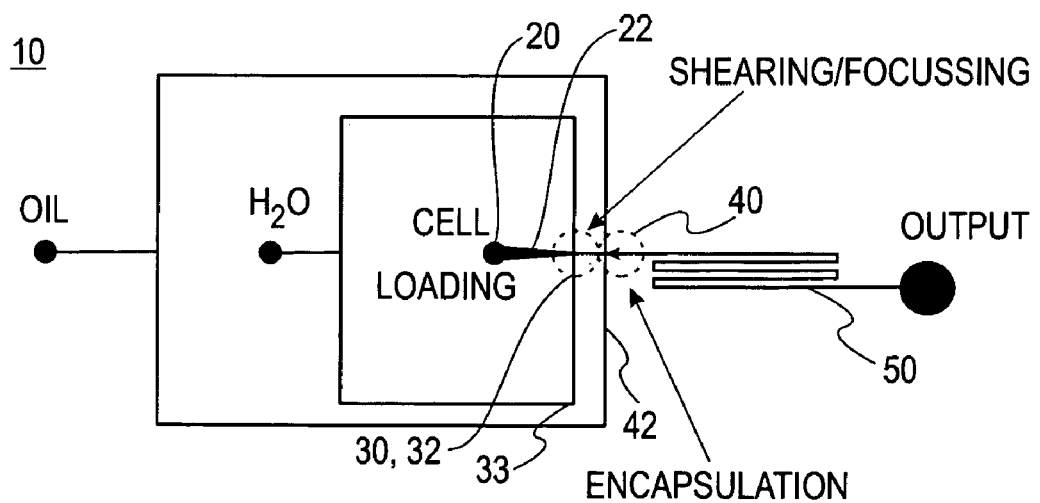
FIG. 2 is a schematic of a microfluidic device of the present invention.

FIG. 2 is a schematic of an exemplary system for encapsulating cells in droplets. The system 10 generally includes a microfluidic device comprising a series of intersecting channels which form a cell loading region 20, a shearing region 30, a focusing region 32, an encapsulation region 40, and a serpentine output 50. As is described further below, the methods of this embodiment can be combined with further functional regions to, for example, obtain polymerized droplets, sort out empty droplets, or combinatorially add biochemical factors. In addition, methods that do not include one or more of the functional regions can also be employed.

As depicted in FIG. 3, polydimethylsiloxane (PDMS) is preferably used as a material for fabricating the microfluidic device. The PDMS used is supplied in two components, a base and a curing agent. The mixture is introduced on top of a silicon wafer formed with photosensitive polymer formed lithographically into the desired channel design. The cell encapsulation zone utilizes mono-dispersed droplets formation designs in PDMS channels molded from SU-8 masters. Other methods of microfluidic device fabrication known in the art can also be used.

The channels of the device are preferably formed of a hydrophobic material such as PDMS or coated with a hydrophobic material such as trimethyl-siloxane. In current systems, the adhesion of cells, cell debris, and cell media components to the walls of the channels is typically overcome by coating the walls of the channel with a hydrophilic coating which prevents the adhesion of proteins. However, such hydrophilic channels cannot be used in multi-phase systems such as those used to create droplets. In the present system, a hydrophobic material such as PDMS is used to prevent the water-cell flow from adhering to the channel walls which could impede shearing of the droplets and result in wide variance in droplet formation or in a complete disruption of the droplet generation. By using the natural hydrophobicity of PDMS or other hydrophobic channel coating, the water-cell flow forms an interfacial geometry with the oil phase that is appropriate for droplet formation and the shearing process can be used to create more uniform droplet sizes.

In preferred embodiments, the channel depth is from 20 μm to 160 μm with widths of about 30 μm to 80 μm, for the cell loading channel 22 and fluid (water and oil) channels 33, 42 (FIG. 2). These dimensions are illustrative of a particular embodiment and can be varied as desired. For example, the channel depth of the cell loading and fluid channels can be non-uniform and range from approximately 10 μm to 180 μm. The widths of the cell loading and fluid channels can also be varied and can be in a range of about 10 μm to 120 μm.

Figure 4:
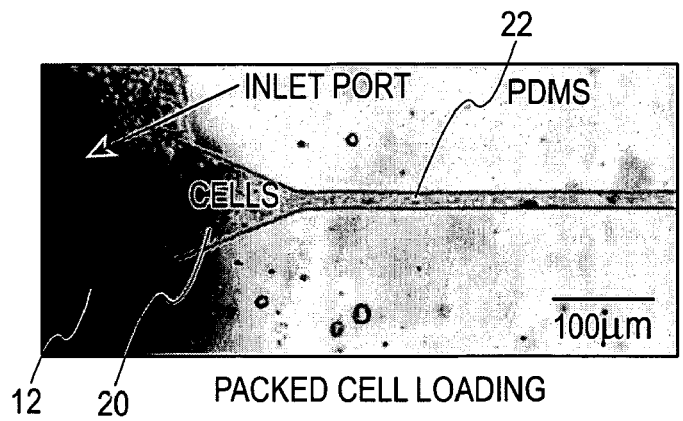
FIG. 4 is a photograph showing packed cell loading in a microfluidic device of the present invention.

Cell loading in the cell loading region 20 can be accomplished in two exemplary methods depending upon the density of the cells. In a first method, cells can be loaded at densities low enough to reduce cell-to-cell adhesion. Since a cluster of about ten cells can approach or exceed the width of the channel, the densities of cells in this method is generally quite low. This can result in a large number of droplets formed which do not contain any cells. Thus, the number of encapsulated cells using this cell loading method is typically small and is generally on the order of approximately zero to five cells per droplet. In an alternative method, a packed cell loading method can be used (FIG. 4). In this method, the cells 12 are allowed to aggregate and are funneled into and forced through the cell loading channel 22 in a stream much like a very viscous fluid. In this embodiment, the number of encapsulated cells will be approximately twenty to fifty cells per droplet. Other methods of cell loading known in the art can also be used. For example, large densities of cells can be used in a media that has a reduced calcium content. The reduced calcium content media helps diminish cell clumping by reducing cell adhesion.

The cells 12 used can comprise any desired cell type or types. The cells 12 can comprise a homogenous set of cells or combine multiple cell types to form heterogeneous droplets. As discussed further below, highly self-adherent cells can be used in conjunction with the device and methods disclosed herein. In addition, non-self-adherent cell types, such as fibroblasts, can also be used.

Figure 6A:
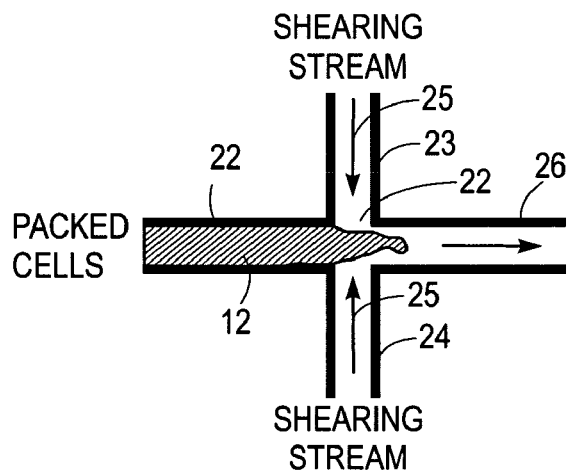
FIG. 6A is a schematic of a shearing region of an exemplary microfluidic device of the present invention.
Figure 5:
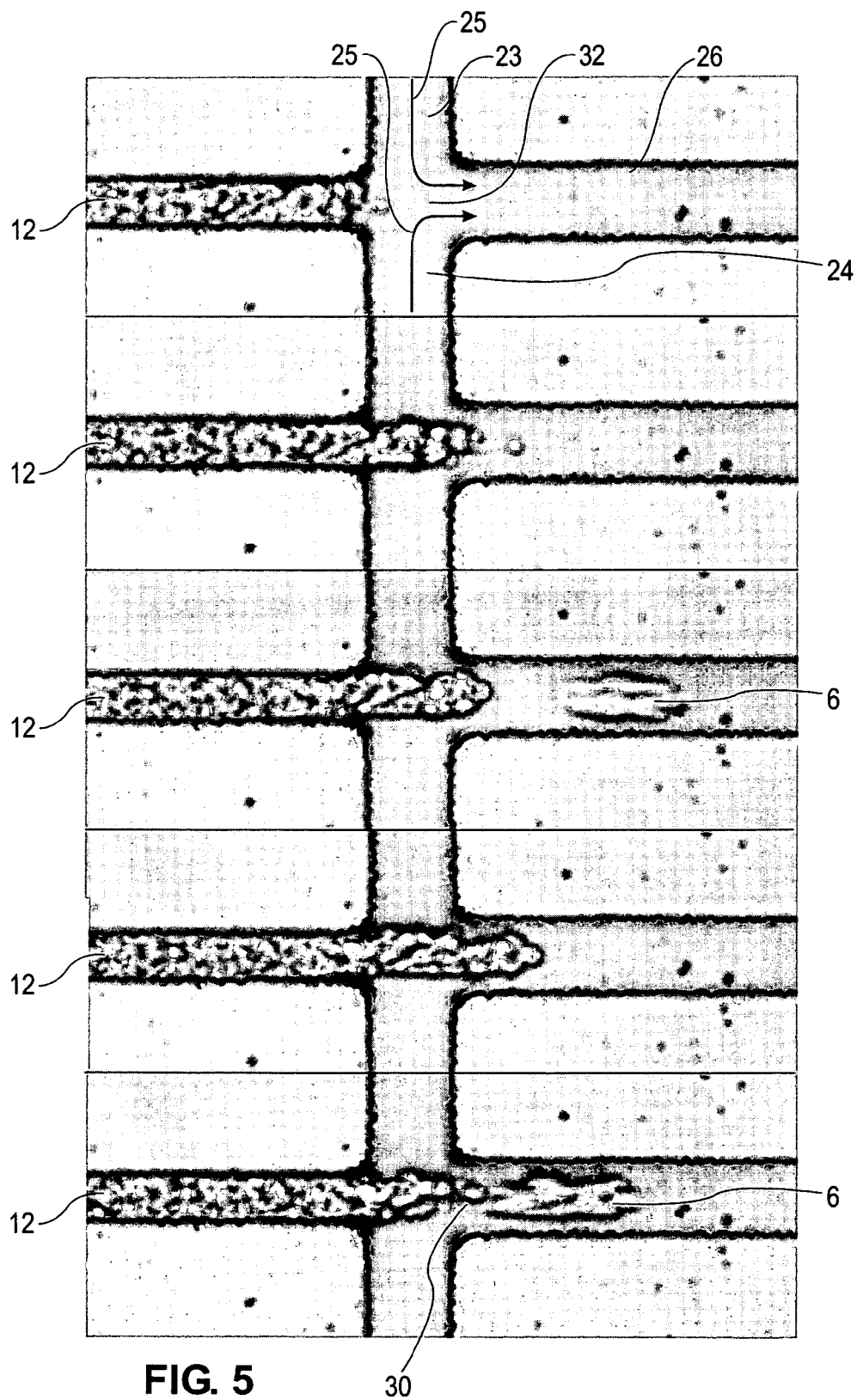
FIG. 5 is a photograph of a shearing region of a microfluidic device of the present invention.

As the cells 12 come out of the cell loading channel 22, they are exposed to shearing streams 25 from a first set of upper and lower channels 23, 24 to form a dual-shear or double shear format (FIGS. 5 and 6A). The shearing streams 25 flowing through the upper and lower channels 23, 24 can comprise a continuous water flow or other aqueous flow. The horizontal force pulling apart the cells 12 is proportional to the length of the stream of cells 12 that is exposed to the shear forces. Therefore, the size of the group of cells or cell clusters 6 that is sheared off into a droplet channel 26 can be regulated by the geometry of the region. For example, the width and/or depth of the cell loading channel 22 can be adjusted to create different sizes of cell clusters 6. In addition, and as discussed further below, the angle of the channels 12, 23, 24 and 26 relative to one another can be adjusted to adjust the forces of the shearing streams 25. In an alternative embodiment, there can be a single water inlet channel or more than two water inlet channels that act upon the cells 12. The flow rates of the channels can be adjusted by means known in the art such as syringe pumps.

Figure 7:
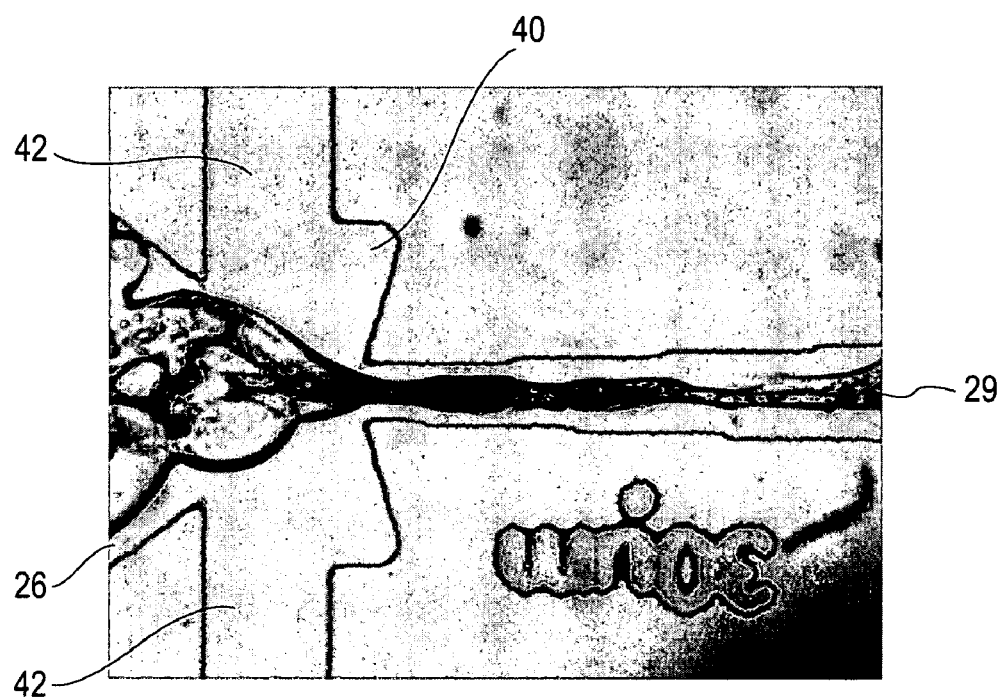
FIG. 7 is a photograph of an encapsulation region of a microfluidic device.

In the focusing region 32, the cells 12 are focused to the center of the droplet channel 26. The focusing region thereby prevents the build-up of cell proteins and cell debris on the channel walls. The effect of adhesion of cell debris and media is shown in FIG. 7. In this figure, cell adhesion has resulted in the inability of the device to generate droplets stably at the encapsulation region 40. As a result, the output flow 29 generates a stream that cannot be used to create droplets.

The focusing region 32 can be upstream of, downstream of, or be combined with the shearing region 30. The focusing region 32 is typically used when the cell type is self-adherent. For cells which are not self-adherent, such as fibroblasts, the focusing region 32 and/or shearing regions 30 can be eliminated if desired.

Figure 9:
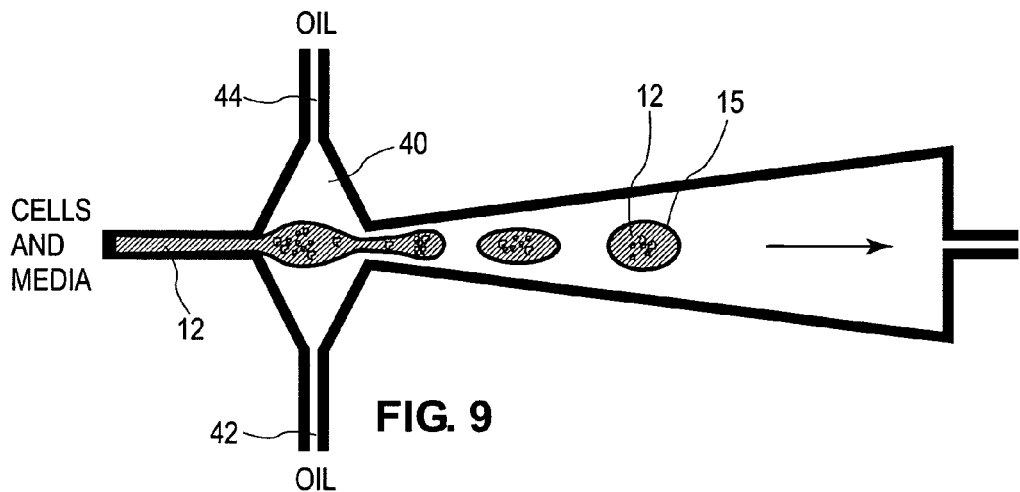
FIG. 9 is a schematic of the encapsulation region of a microfluidic device of the present invention.
Figure 10:
FIG. 10 is a photograph of the encapsulation region of a microfluidic device of the present invention demonstrating encapsulation of a single cell.
Figure 11:
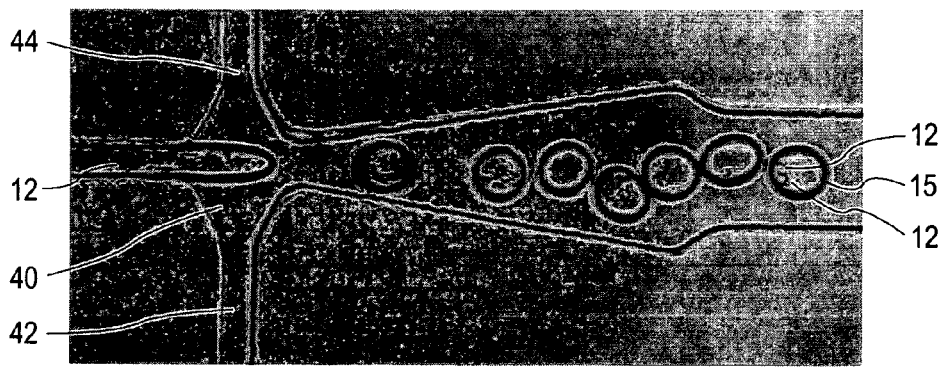
FIG. 11 is a photograph of the encapsulation region of a microfluidic device of the present invention demonstrating encapsulation of multiple cells.
Figure 14A:
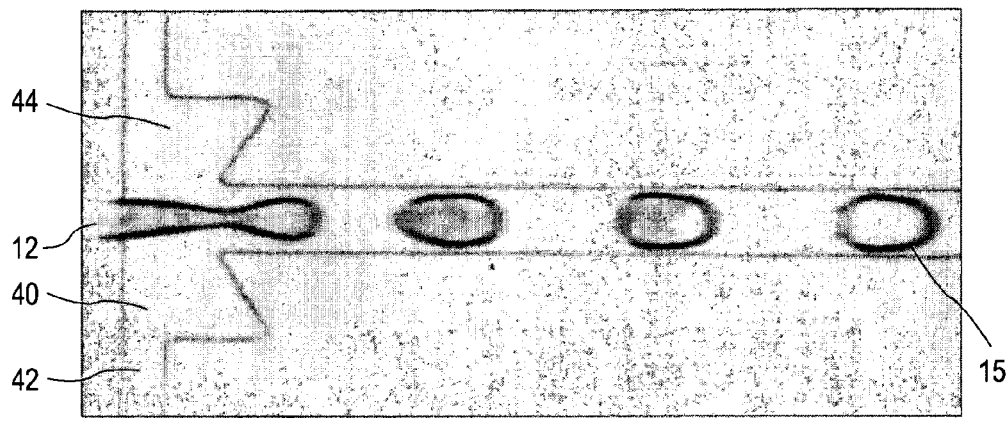
FIGS. 14A and 14B are photographs of encapsulation region of a microfluidic device of the present invention demonstrating encapsulation of multiple adhered cell clusters.
Figure 14B:
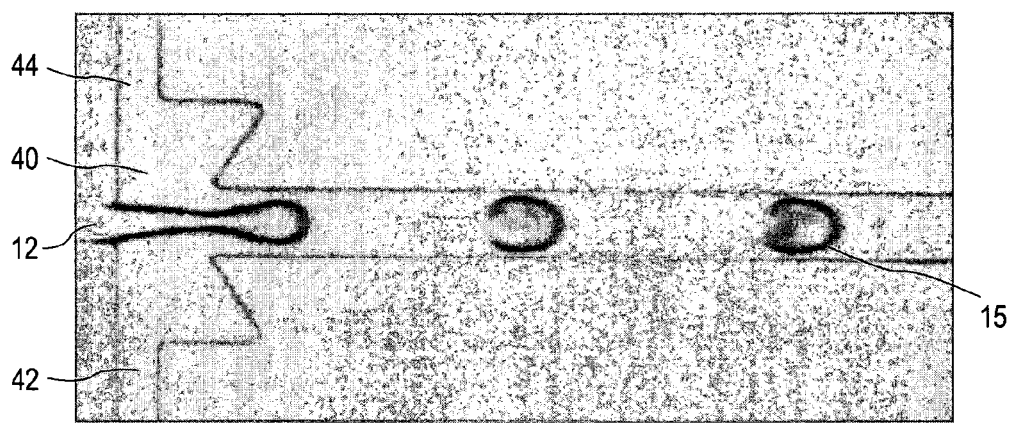

In the cell encapsulation region 40, as shown in FIG. 9, the cell flow is sheared off into discrete droplets 15 by the flow of oil streams from upper and lower oil channels 42, 44. Oil flows from the upper and lower channels 42, 44 to pinch off droplets 15 containing cells 12 and cell media. Cells 12 can be encapsulated singly (FIG. 10), in adherent clusters, or multiple discrete cells 12 can be encapsulated into a single droplet (FIGS. 11 and 12). The system is able to generate droplets 15 containing a similar number of cells 12 per droplet 15 (FIG. 13A). FIGS. 13B-D show three droplets 15 containing a similar number of cells 12.

Figure 8C:
FIG. 8C is a photograph of the shearing region of a three-dimensional flow device of the present invention.
Figure 8A:
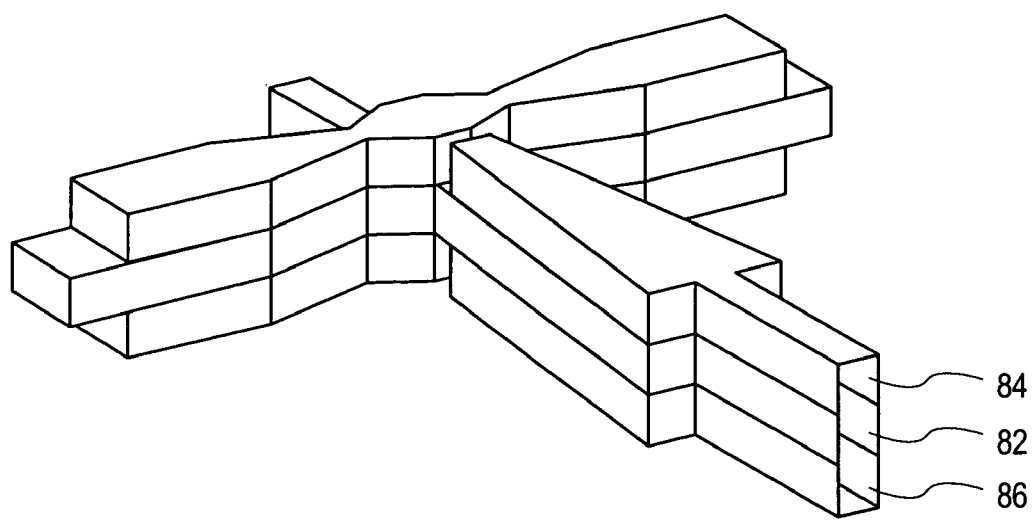
FIG. 8A is a schematic of a three-dimensional flow device of the present invention.
Figure 8B:
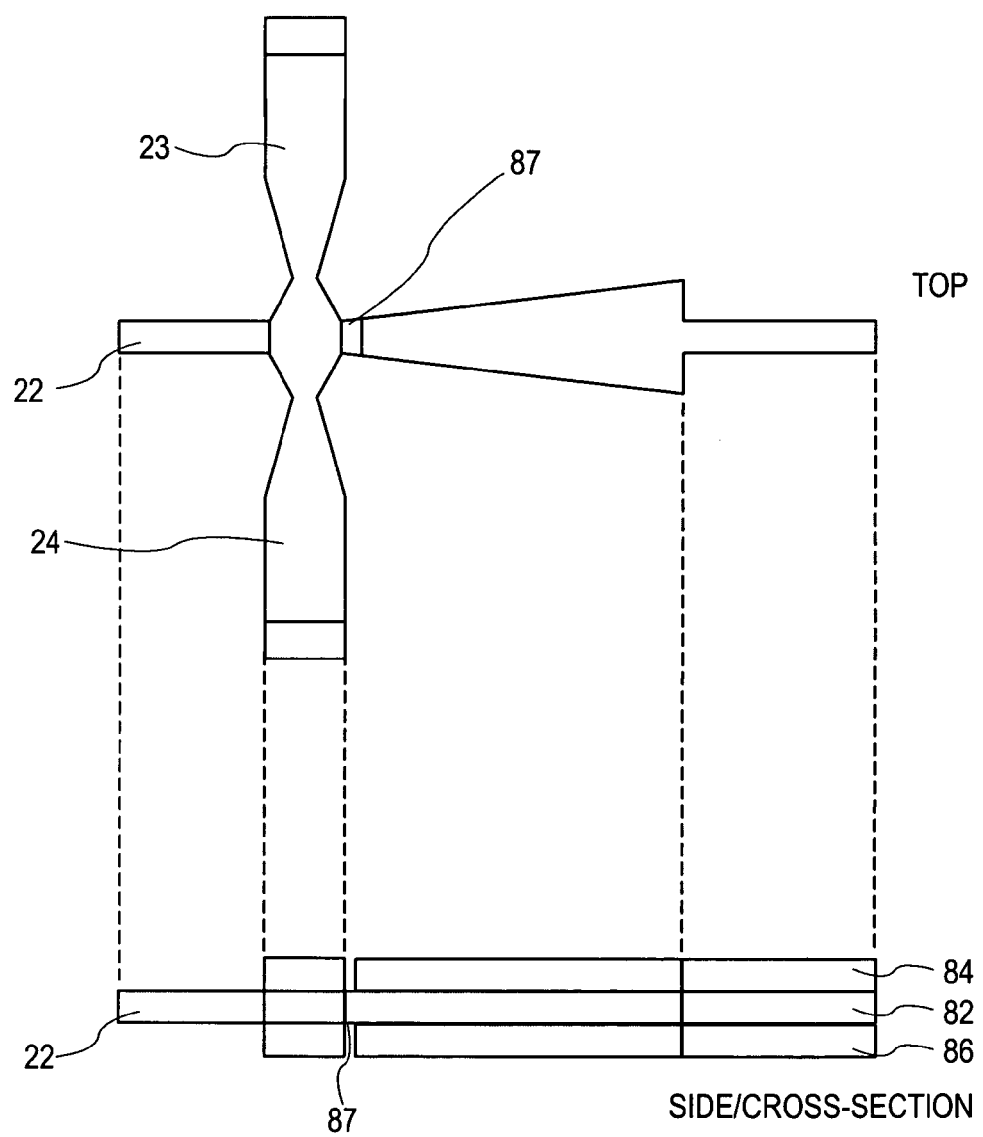
FIG. 8B is a top view and cross-sectional view of the device of FIG. 8A.

The channels 42, 44 can have a variety of configurations such as those shown in FIGS. 11-14. As discussed further below, alternative embodiments of the present system can be used which generate more uniform cell clusters 6 and thereby provide even greater control over the number of cells per droplet 15. For example, the microfluidic device can be configured to create a three-dimensional flow of fluids such as water and/or oil. In this embodiment, the device is initially fabricated to include a middle channel layer 82 and a top channel layer 84 (FIG. 8A) formed on a single wafer using the methods disclosed above in relation to FIG. 3. A bottom channel layer 86 is fabricated on a separate wafer. The combined middle-top channel layer 82, 84 is then sandwiched to the bottom channel layer 86 and fixed to the bottom channel layer 86 by means known in the art. The design combines the ease of fabrication with the advantages of three-dimensional channels. This design can prevent many of the protein adhesion problems that plague two-phase (water/oil) cell devices. In a preferred embodiment, the channel comprises a downstream necked region 87, which further reduces adhesion and facilitates creation of uniform sizes of cell clusters and droplets (FIGS. 8B and 8C).

In methods using packed cell loading, the number of cells 12 per droplet 15 is generally on the order of approximately twenty to fifty cells per droplet. The diameter of the droplets formed can be in the range of 20 μm to 175 μm. Since the channel depth is typically around 40 μm and some droplet diameters are in the range of 100 μm or more, the droplets 15 shown are not spherical, but rather a squat cylindrical shape. If allowed to expand, the droplets 15 would generally form spheres in the range of 60 μm to 175 μm, with the smallest cell-containing droplets 15 measured to be about 20 μm in diameter.

The encapsulation of the cells can be either temporary or permanent. Temporary isolation allows the cells to be exposed to discrete concentrations of chemicals or factors and then cultured again. Permanent encapsulation involves the addition of polymers to the droplet flow. The gelation agents for the polymers can be introduced in one of three manners: (1) a secondary droplet population is generated and induced to fuse with the cell capsules; (2) the cell droplets will be extracted into a water phase stream containing the polymerization agent established parallel to the oil phase; or (3) gelation agents are dissolved directly into the oil phase. This type of polymer encapsulation is the basis for many developing cell-based therapies such as islet-cell implantation. The ability to encapsulate cells on a microfluidic platform in both permanent (polymerized capsule) and a temporary (simple, immiscible fluid separation) manners will have applications in many cell culturing, cell-base therapy, and cell assay methods. For example, in cell culturing small groups of cells (~5 cells, or 20-50 cells) can be isolated from one another and distributed for further culturing. In the case of single cells, this would be equivalent to replating at clonal density, but could be processed in an automated and complex fashion. In the case of multiple cells, droplets containing different types of cells could be fused (in a combinatorial fashion) and cultured to produce cell populations beginning from precisely-defined, heterogeneous initial conditions. Furthermore, several mechanical and transport properties of the capsules scale inversely with capsule diameter (i.e. properties improve with smaller diameters), which at present can only be generated through microfluidics.

In cell-based therapy, polymerized capsules can be applied to cell based therapies. For example, the capsules can provide immuno-protection to the cells after transplantation. With the device of the present invention, the protective polymer encapsulation can provide smaller capsule size, with corresponding improvements in structural properties; more uniform mixing and reaction times; and the possibility to incorporate further microfluidic processing both upstream and downstream of the encapsulation area.

In one experimental protocol using the microfluidic device described above, rat neuroblastoma cells [B103] were captured in droplets having a diameter less than 100 μm in a continuous process that allowed for various technologies (e.g. combinatorial delivery of drugs to cells, polymerization of droplet, etc.) to be incorporated on-chip, downstream of the encapsulation region. The [B103] cells were first cultured and then resuspended in new media. In this experiment, the droplet generation was initially established using only the oil and water flows, so that the generation was stabilized before the addition of the cells. This prevented the deposition of proteins, carbohydrates, and cell debris on the channel walls, which would change the surface energy from hydrophobic to hydrophilic and inhibit droplet formation.

Figure 15:
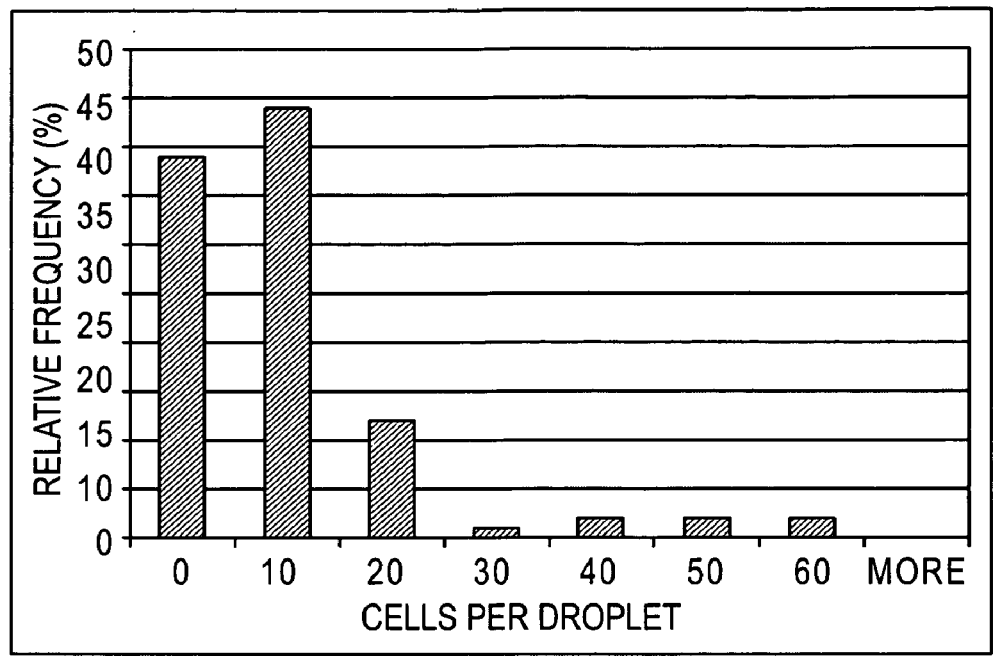
FIG. 15 is a chart depicting the number of cells encapsulated per droplet based on an experimental protocol using the device and methods of the present invention.

The cells were then injected into a cell inlet port. Syringe pumps provided flow rates to the oil, water, and cell inlet channels of 3.0 μl/min, 1.6 μl/min, and 0.5 μl/min, respectively. The encapsulation of the cells was recorded using a high-speed camera and the number of cells per droplet was calibrated to the grayscale of the images and estimated via software. As depicted in FIG. 15, the number of cells that were encapsulated per droplet was fairly consistently regulated. The water flow remained continuous during the droplet formation process to stabilize and maintain the droplet generation. Therefore, it was reasonable to expect that a percentage of the droplets would contain no cells. However, of the droplets that did contain cells, almost ninety percent of the droplets contained between one and twenty cells, thereby avoiding the disruption of the droplet generation process caused by huge clusters of cells.

Figure 6B:
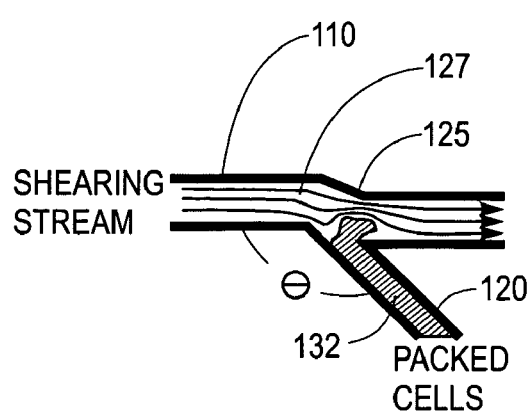
FIG. 6B is a schematic of a shearing region of alternative exemplary embodiment of a microfluidic device of the present invention.
Figure 16:
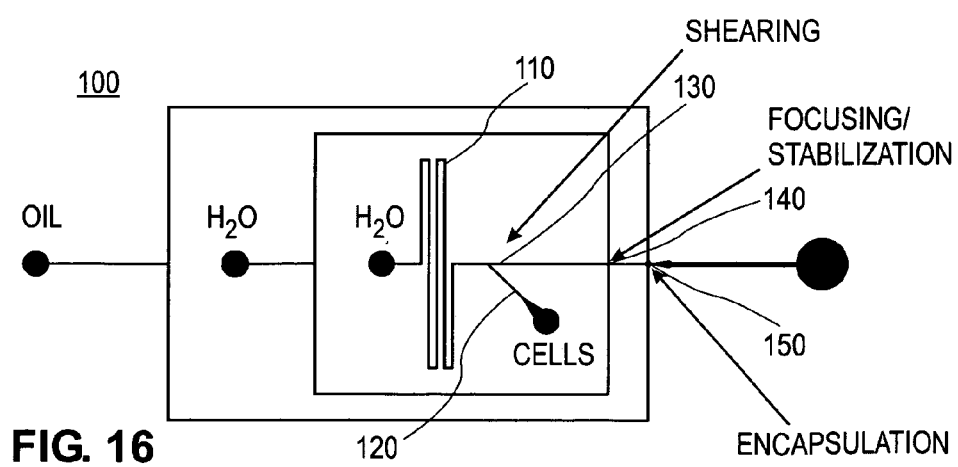
FIG. 16 is a schematic of an alternative embodiment of a microfluidic device of the present invention.

In a further embodiment, the cells can be introduced into a water flow via a downstream cell loading channel 120 that is disposed at an obtuse angle θ relative to the water input channel 110 (FIGS. 6B and 16). Typically the water input channel 110 comprises a series of serpentine switchbacks to ensure that the pressure gradient maintains a downstream flow towards the output. The cells can be loaded as described above via a low density method, packed cell method, or other method known in the art. If polymerization of the droplet 15 is desired, alginate or a similar material can be added to the cell media.

Figure 17A:
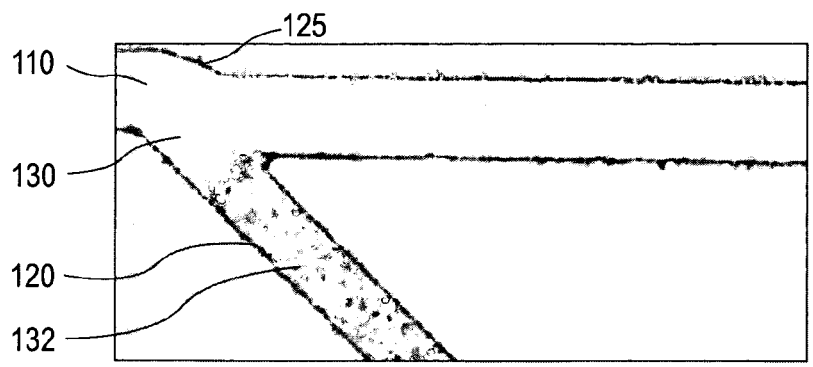
FIG. 17A-D are photographs of the shearing region of an alternative embodiment of a microfluidic device of the present invention.
Figure 17B:
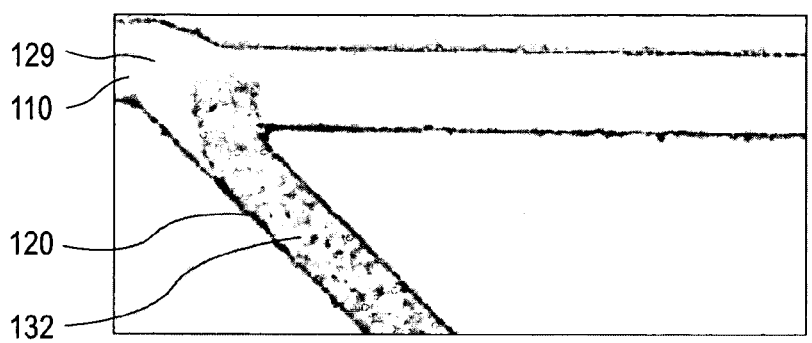
Figure 17C:
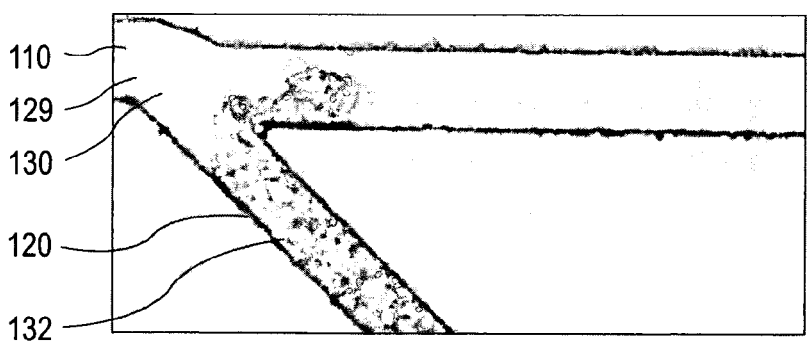
Figure 17D:
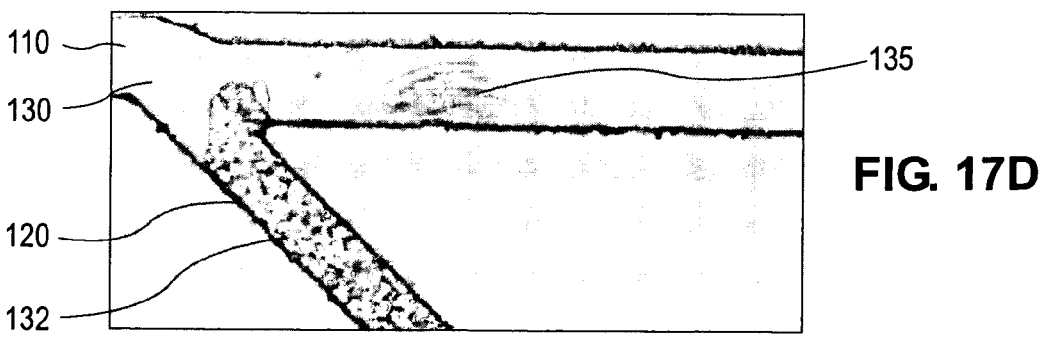
Figure 24:
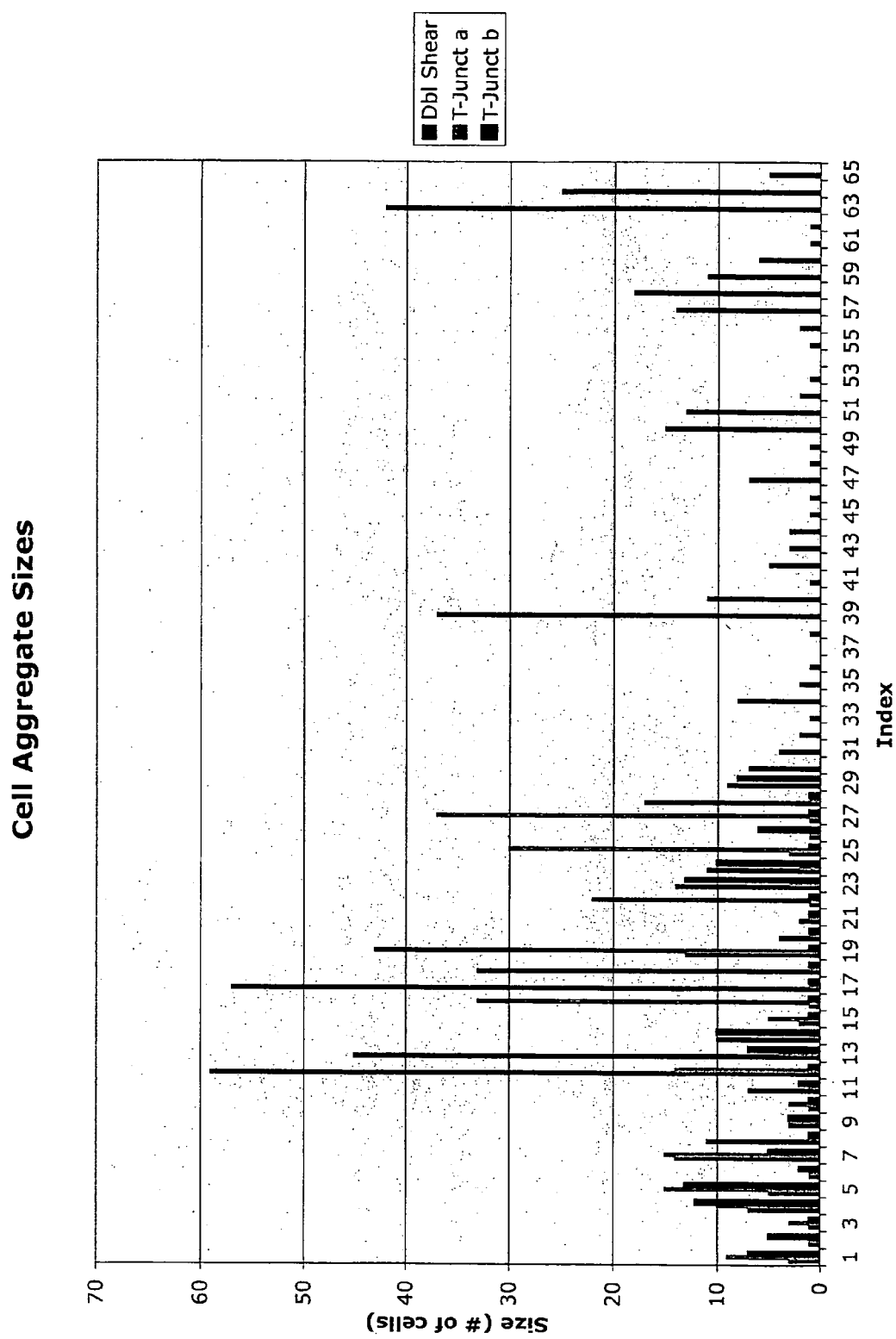
FIG. 24 is a chart showing cell aggregate sizes using t-junction and using a double shear method.

In this embodiment, the size of the cell cluster can be controlled to a greater extent than in the dual-shear embodiment disclosed above. The angled, t-junction entry of the cell loading channel 120 allows for shearing of the packed cells 132 as shown schematically in FIG. 6B. FIG. 17A shows a set of packed cells 132 at a shearing region 130 of the microfluidic device 100. The junction 129 of the two channels can include a slightly depressed region 125 that is used to focus the shearing stream 127 of the water flow. This further allows control over the size of the droplet 15. As the packed cells are displaced farther into the junction region 129, the force of the shearing streams 127 begins to separate a portion of the packed cells 132 (FIG. 17B). In FIG. 17C, the shearing stream 127 has nearly separated a portion of the packed cells 132 and in FIG. 17D a discrete portion 135 of the packed cells 132 has been sheared from the packed cells 132. This process is then repeated to form additional cell clusters for droplet encapsulation. As shown in FIG. 24, the size of the cell clusters formed using a t-junction are generally more uniform than the droplet size using the double shear method.

The present embodiment can further comprise a focusing or stabilization region 140 that focuses the cell clusters to the center portion of the channel to prevent adhesion of the cells to the channel walls as described above (FIG. 16). In the next step, the cell clusters enter an encapsulation region 150 in which one or more channels of oil flow are introduced to encapsulate the cell clusters. In a further embodiment, the system can comprise a polymerization step in which, for example, one or more channels with a calcium-oil flow are introduced to polymerize the droplet.

Figure 18:
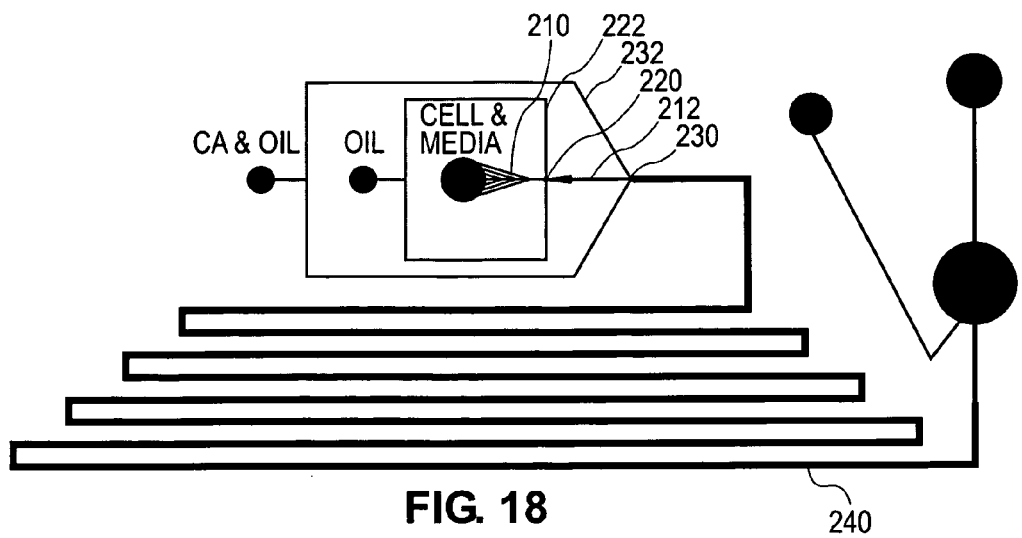
FIG. 18 is a schematic of another alternative embodiment of a microfluidic device of the present invention.

In yet a further exemplary embodiment, the microfluidic device can be used to generate polymerized cells (FIG. 18). In one embodiment, the device 200 comprises a cell loading region 210, an encapsulation region 220, a polymerization region 230, and a series of serpentine switchbacks 240. The techniques for polymerization can be combined with the methods disclosed above, or can be used in isolation. For example, the functional regions for cell loading and shearing/focusing discussed above can be added to the present system if desired. Cells are initially loaded with phosphate buffer solution (PBS) and/or media in the cell loading region 210. For polymerization, alginate or a similar material is used. In one exemplary embodiment, equal parts of 4% alginate dissolved in PBS was combined with cells also in PBS to produce an end combination of 2% alginate in PBS. Full cell media with alginate can also be used. Other polymerization agents and/or cell-media combinations known in the art can also be used.

The cells then pass through a downstream cell encapsulation region 220. As with the methods disclosed above, the cell encapsulation region 220 comprises one or more channels 222 of oil flow. The cell flow is sheared off into droplets by the flow of oil streams from the upper and lower oil channels 222. Oil flows from the upper and lower channels 222 pinching off droplets containing cells and cell media to form encapsulated cells in droplets.

Figure 19:
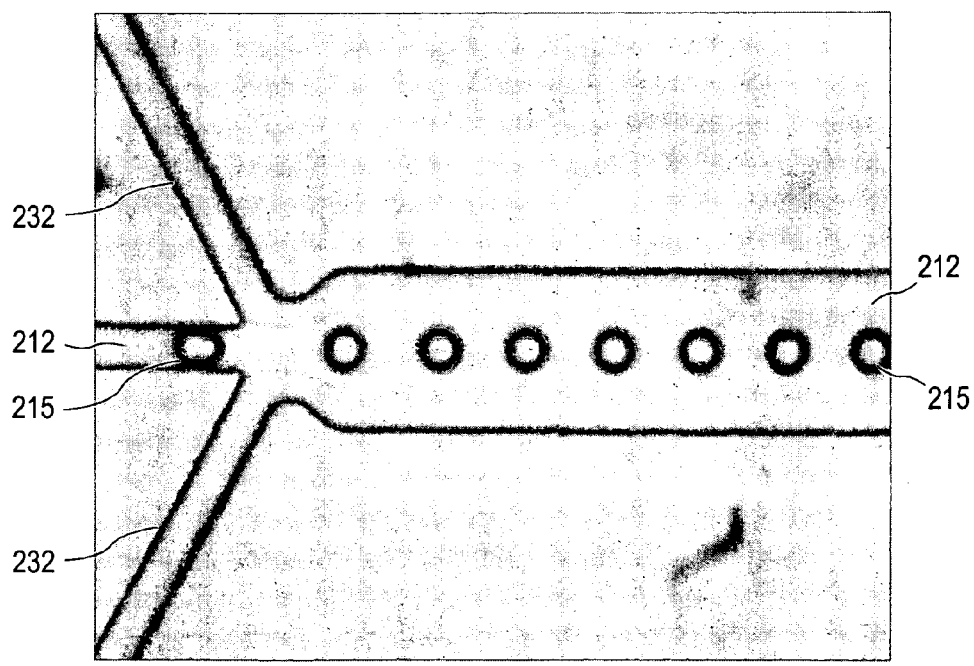
FIG. 19 is a photograph of the polymerization region of a microfluidic device of the present invention.
Figure 20:
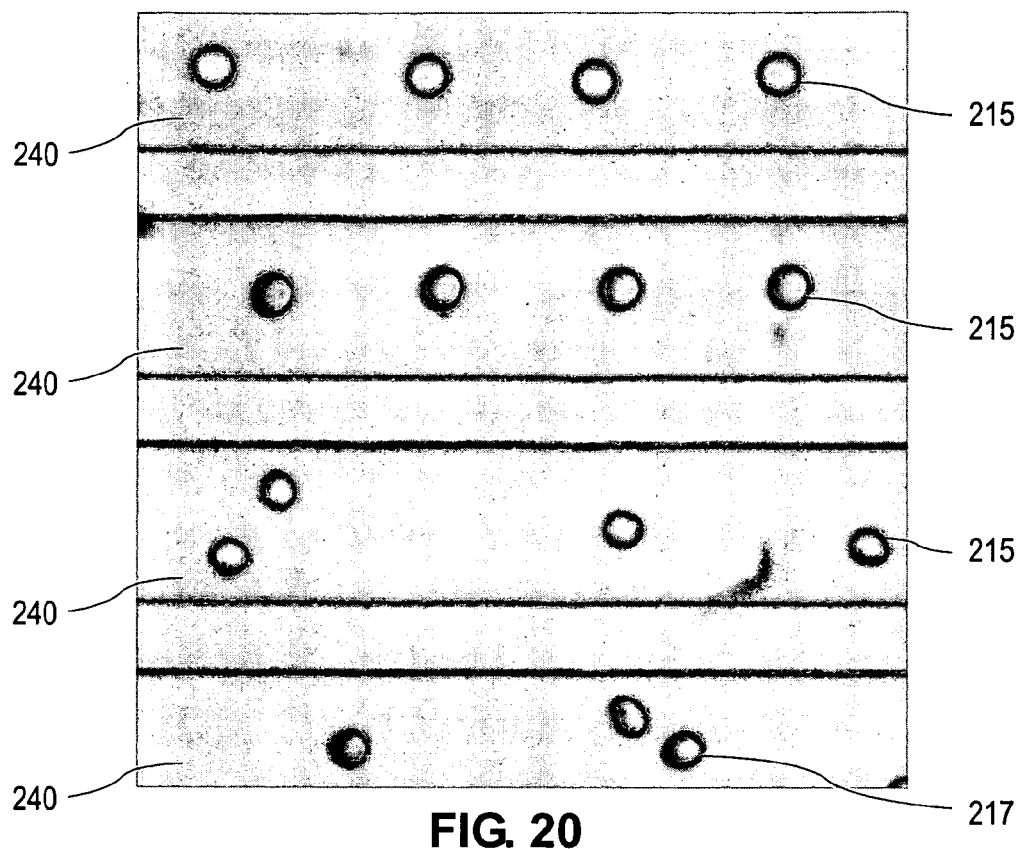
FIG. 20 is a photograph of the serpentine switchbacks of a microfluidic device of the present invention.

Downstream from the encapsulation region, two inlet channels 232 comprising calcium and oil are flowed to intersect with the central channel 212 (FIG. 19). A surfactant, such as dodecylbenzenesulfonic acid (DBSA), is used to dissolve the calcium in the oil. The calcium diffuses into the droplet 215 and forms bonds between individual alginate chains, crosslinking the monomer and forming a uniform, "solid" polymer bead surrounding the cells (FIGS. 19 and 20). The calcium-oil input channels 232 can be angled at any desired angle relative to the central channel 212. The flow rates and geometries of the system are typically designed such that the act of polymerization does not rip the droplet apart or severely distort the spherical shape of the droplet.

Figure 23:
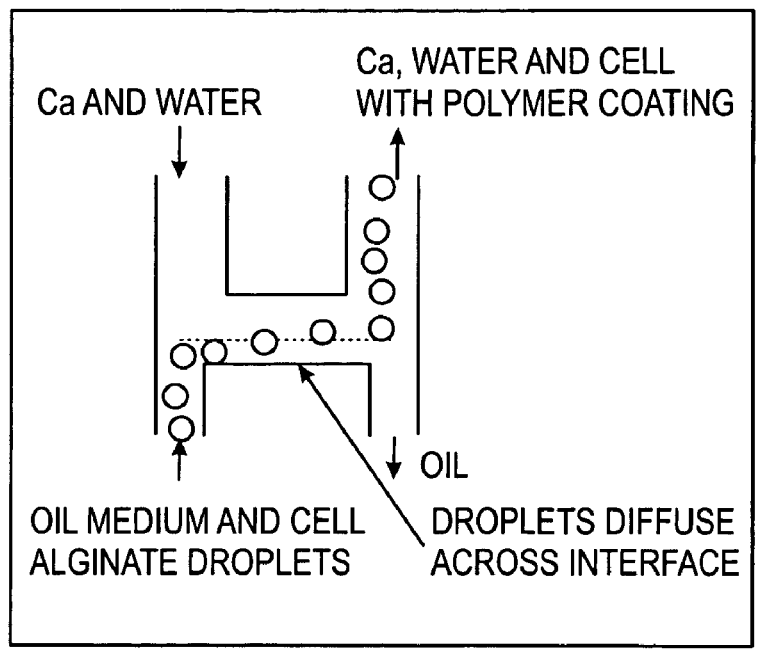
FIG. 23 is a schematic an immiscible phase, parallel extraction filter.
Figure 21:
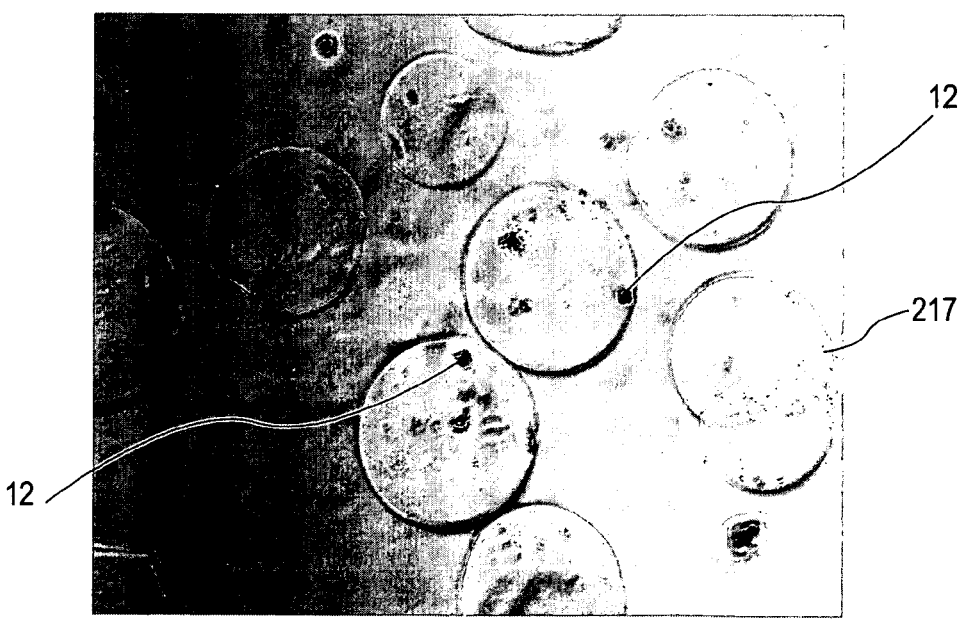
FIG. 21 is a photograph of alginate beads encapsulating cells resuspended in water formed by methods of the present invention.
Figure 22:
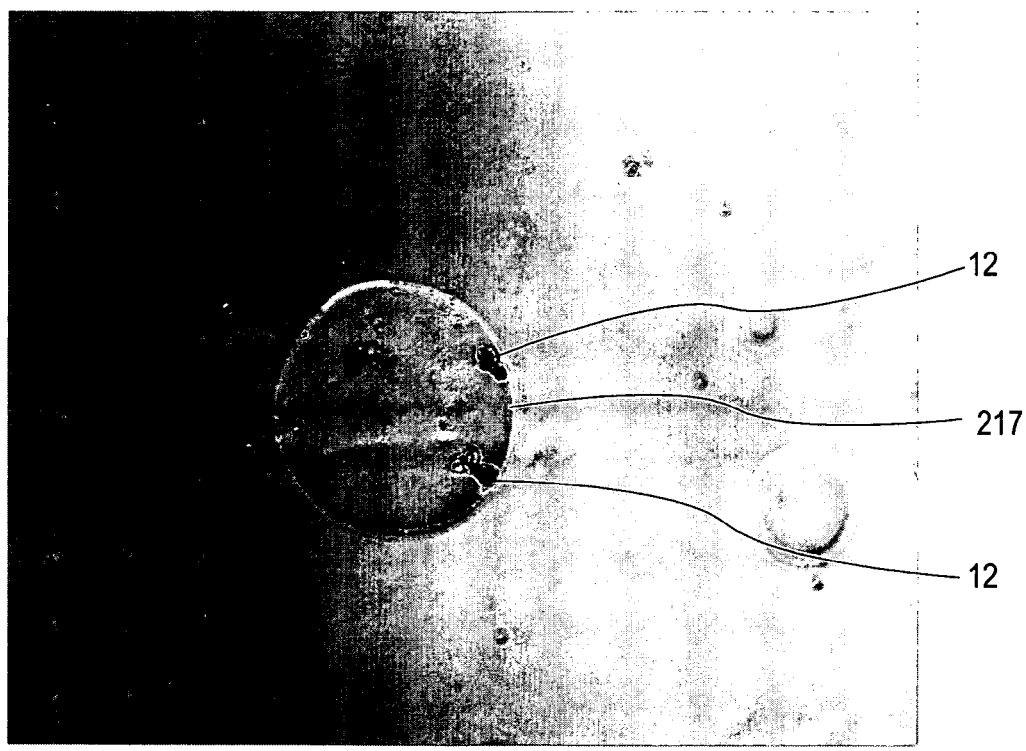
FIG. 22 is a photograph of alginate beads encapsulating cells resuspended in water formed by methods of the present invention.

As the droplets continue downstream along the switchbacks of the serpentine channel 240, the alginate gradually polymerizes and forms an alginate bead 217. FIG. 20 shows the progression of the alginate polymerization. The top of the figure shows a droplet 215 that has just entered the serpentine switchbacks 240. The droplets 15 in this stage comprise a larger volume of water as compared to the more highly polymerized droplets in the channel at the bottom of the figure. If desired, the polymerized droplets which have formed alginate beads 217 can be returned to water (FIGS. 21 and 22). This demonstrates that the polymerization/encapsulation is permanent and not dependent on the oil phase. Droplets can also be polymerized using various on-chip techniques, two of which are droplet fusion and parallel-stream recovery. Cells in alginate droplets and calcium droplets can be prepared in two different channels on the same device (or chip). At a junction, the droplets collide to produce cell droplets with polymer coating. Referring to FIG. 23, for parallel-stream recovery, the oil stream with the droplets containing cells and alginate, runs parallel to a water stream with calcium. As the droplets pass the interface between the streams the droplets are polymerized.

In the foregoing specification, the invention has been described with reference to specific embodiments thereof. It will, however, be evident that various modifications and changes may be made thereto without departing from the broader spirit and scope of the invention. For example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed:

1. A cell encapsulation microfluidic device having a plurality of intersecting channels and a plurality of inputs coupled to the channels for inputting cells and fluids into the plurality of channels, comprising,
a cell loading region comprising a cell loading channel having a first end into which a plurality of cells are introduced, and a second end through which the plurality of cells pass, the first end having a funnel shaped inlet adapted to aggregate the plurality of cells at the first end of the cell loading channel and force the plurality of cells through the cell loading channel in a stream;
a shearing region comprising opposing flow first and second shearing stream channels intersecting with the cell loading channel at the second end of the cell loading channel and a droplet channel intersecting at a first end with the first and second shearing stream channels adjacent the intersection of the first and second shearing stream channels and the cell loading channel and the droplet channel extending from the intersection of the first and second shearing stream channels and the cell loading channel, wherein flow of a first fluid through the first and second shearing channels intersects the stream of the plurality of cells from the cell loading channel and shears off one or more cells from the stream of plurality of cells into the droplet channel and the sheared off one or more cells being carried by the first fluid through the droplet channel, and
an encapsulation region comprising opposing flow third and fourth shearing stream channels intersecting with the droplet channel at a second end of the droplet channel downstream from the shearing region and a serpentine outlet channel intersecting the third and fourth shearing stream channels adjacent the intersection of the third and fourth shearing stream channels and the end of the droplet channel and the serpentine outlet channel extending from the intersection of the third and fourth shearing stream channels and the end of the droplet channel, wherein flow of a second fluid through the third and fourth shearing channels intersects the flow of the first fluid and one or more cells being carried by the first fluid from the droplet channel to shear off and encapsulate droplets of the first fluid containing one or more cells, wherein the serpentine channel comprising a plurality of channel switchbacks.

2. The device of claim 1, further comprising a polymerization zone interposing the encapsulation region and the serpentine outlet channel, wherein an encapsulation channel intersecting the third and fourth shearing stream channels adjacent the intersection of the third and fourth shearing stream channels and the end of the droplet channel and the encapsulation channel extending from the intersection of the third and fourth shearing stream channels and the end of the droplet channel, the polymerization region comprising opposing flow fifth and sixth fluid channels intersecting the encapsulation channel at an end of the encapsulation channel downstream from the encapsulation region and intersecting the serpentine outlet channel, wherein flow of a third fluid through the fifth and sixth fluid channels intersects the flow of the second fluid from the encapsulation channel.

* * * * *